(12) United States Patent
Swanson

(10) Patent No.: US 10,741,910 B2
(45) Date of Patent: Aug. 11, 2020

(54) INTEGRATED PHOTONIC ARRAY FED BY FREE-SPACE OPTICS

(71) Applicant: Eric Swanson, Gloucester, MA (US)

(72) Inventor: Eric Swanson, Gloucester, MA (US)

( * ) Notice: Subject to any disclaimer, the term of this patent is extended or adjusted under 35 U.S.C. 154(b) by 225 days.

(21) Appl. No.: 16/018,537

(22) Filed: Jun. 26, 2018

(65) Prior Publication Data

US 2019/0006753 A1     Jan. 3, 2019

Related U.S. Application Data

(60) Provisional application No. 62/525,783, filed on Jun. 28, 2017.

(51) Int. Cl.

| | | |
|---|---|---|
| *G02F 1/01* | (2006.01) | |
| *H01Q 3/26* | (2006.01) | |
| *G02B 27/00* | (2006.01) | |
| *H01S 3/067* | (2006.01) | |
| *A61B 1/00* | (2006.01) | |
| *G01S 17/89* | (2020.01) | |
| *G01S 7/481* | (2006.01) | |
| *A61B 5/00* | (2006.01) | |

(52) U.S. Cl.
CPC ......... *H01Q 3/2676* (2013.01); *A61B 1/0017* (2013.01); *A61B 1/00096* (2013.01); *A61B 5/0066* (2013.01); *A61B 5/0084* (2013.01); *G01S 7/4817* (2013.01); *G01S 17/89* (2013.01); *G02B 27/0087* (2013.01); *H01S 3/067* (2013.01)

(58) Field of Classification Search
USPC ........................................................ 359/279
See application file for complete search history.

(56) References Cited

U.S. PATENT DOCUMENTS

2014/0376000 A1* 12/2014 Swanson ............... H01S 3/1003
356/479

FOREIGN PATENT DOCUMENTS

| EP | 0981733 | 11/2004 |
| EP | 0883793 | 11/2007 |
| EP | 1839375 | 4/2014 |

OTHER PUBLICATIONS

James G. Fujimoto, Eric Swanson, Robert Huber, European Inventor Award 2017, Jun. 15, 2017, 3 pages. PRWeb.

(Continued)

*Primary Examiner* — James C. Jones
(74) *Attorney, Agent, or Firm* — Rauschenbach Patent Law Group, LLC; Kurt Rauschenbach

(57) ABSTRACT

An optical system for producing an optical probe beam includes an optical source that generates a free-space optical beam. An optical element is positioned in a path of the free-space optical beam to project the free-space optical beam to generate a projected free-space optical beam. A photonic integrated phased-array component positioned in a path of the projected free-space optical beam to reflect the projected free space optical beam, thereby generating the optical probe beam. The photonic integrated phased-array component comprises a plurality of antenna elements and a substrate positioned proximate to the plurality of antenna elements, wherein the substrate includes a plurality of fan-out electrical connections from at least some of the plurality of antenna elements such that a size of a region comprising the fan-out electrical connections is larger than a size of a region comprising the plurality of antenna elements.

25 Claims, 4 Drawing Sheets

(56) References Cited

OTHER PUBLICATIONS

Warren L Stutzman and Gary A. Thiele, "Antenna Theory and Design", Chapter 3, pp. 108-169, John Wiley & Sons, ISBN 0-471-04458-X, 1981. Textbook.
Jie Sun, Erman Timurdogan, Ami Yaacobi, Zhan Su, Ehsan Shah Hosseini, David B. Cole, and Michael R. Watts, "Large-Scale Silicon Photonic Circuits for Optical Phased Arrays", IEEE Journal of Selected Topics in Quantum Electronics, vol. 20, No. 4, Jul./Aug. 2014.
Jie Sun, Ehsan Shah Hosseini, Ami Yaacobi, David B. Cole, Gerald Leake, Douglas Coolbaugh, and Micheael R. Watts, "Two-dimensional apodized silicon photonic phased arrays", Optics Letters, vol. 39, No. 2, Jan. 15, 2014.
C. T. DeRose, R. D. Kekatpure, D. C. Trotter, A. Starbuck. J. R. Wendt, A. Yaacobi, M. R. Watts, U. Chettiar, N. Engheta, and P. S. Davids, "Electronically controlled optical beam-steering by an active phased array of metallic nanoantennas", Optics Express, vol. 21, No. 4, Feb. 25, 2013.
Jie Sun, Erman Timurdogan, Ami Yaacobi, Ehsan Shah Hosseini, and Michel R. Watts, "Large-scale nanophotonic phased array", Nature, vol. 493, Jan. 10, 2013.
Ami Yaacobi Erman Timurdogan, and Michael R. Watts, "Vertical emitting aperture nanoantennas", Optics Letters, vol. 37, No. 9, May 1, 2012.
J. K. Doylend, M. J. R. Heck, J. T. Bovington, J. D. Peters, L. A. Coldre, and J. E. Bowers, "Two-dimensional free-space beam steering with an optical phased array of silicon-on-insulator", Optics Express, vol. 19, No. 22, Oct. 24, 2011.
Karel Van Acoleyen, Hendrick Rogier, and Roel Baets, "Two-dimensional optical phased array antenna on silicon-on-insulator", Optics Express, vol. 18, No. 13, Jun. 21, 2010.
M. Raval, C. Poulton, and M. R. Watts, "Unidirection waveguide grating antennas with uniform emission for optical phased arrays", Optics Letters, v. 42, No. 12, doi: 10.1364/OL42.002563, 2017.
A. Femius Koenderink, Andrea Alù, Albert Polman, "Nanophotonics: Shrinking light-based technology", Science, v. 348, No. 6234, doi: 10.1126/science.1261243, 2015.
Mikhail I. Shalaev, Jingbo Sun, Alexander Tsukernik, Apra Pandey, Kirill Nikolskiy, and Natalia M. Litchinitser, "High-Efficiency All-Dielectric Metasurfaces for Ultracompact Beam Manipulation in Transmission Mode", Nano Letters, 15 (9), pp. 6261-6266, doi: 10.1021/acs.nanolett.5b02926, 2015.
Paul J. M. Suni, John Bowers, Larry Coldren, S.J. Ben Yoo, "Photonic Integrated Circuits for Coherent Lidar", 18th Coherent Laser Radar Conference, CLRC 2016, Jun. 26-Jul. 1, 2016.
Chao Li, Huijuan Zhang, Mingbin Yu, and G. Q. Lo, "CMOS-compatible High Efficiency Double-Etched Apodized Waveguide Grating Coupler", Opt. Expr., 21, pp. 7868, 2013.
Christopher Vincent Poulton, "Integrated LIDAR with Optical Phased Arrays in Silicon Photonics", MIT MS EECS Thesis, Sep. 2016.
S. J. Ben Yoo, Binbin Guan and Ryan P. Scott, "Heterogeneous 2D/3D Photonic Integrated Microsystems", Microsystems & Nanoengineering, v. 2, 16030; doi:10.1038/micronano.2016.30, 2016.
Francesco Aieta, Patrice Genevet, Nanfang Yu, Mikhail A. Kats, Zeno Gaburro, and Federico Capasso. "Out-of-Plane Reflection and Refraction of Light by Anisotropic Optical Antenna Metasurfaces with Phase Discontinuities", Nano Lett., 12 (3), pp. 1702-1706, doi: 10.1021/nl300204s, 2012.
Paul F. McManamon, Philip J. Bos, Michael J. Escuti, Jason Heikenfeld, Steve Serati, Huikai Xie, Edward A. Watson , "A Review of Phased Array Steering for Narrow-Band Electrooptical Systems", Proc. of the IEEE, 97, pp. 1078, doi: 10.1109/JPROC. 2009.2017218, 2009.
Byung-Wook Yoo, Mischa Megens, Tianbo Sun, Weijian Yang, Connie J. Chang-Hasnain, David A. Horsley, and Ming C. Wu, "A 32x32 Optical Phased Array Using Polysilicon Sub-Wavelength High-Contrast-Grating Mirrors", Opt. Expr., 22, doi:10.1364/OE. 22.019029, 2014.
Weihua Guo, Pietro R. A. Binetti , Chad Althouse , Milan L. Mašanović, Huub P. M. M. Ambrosius, Leif A. Johansson, Larry A. Coldren, "Two-Dimensional Optical Beam Steering with InP-based Photonic Integrated Circuits," IEEE J. Sel. Topics Quantum Electron., Special Issue on Semiconductor Lasers, 19, pp. 6100212, 2013.
J. C. Hulme, J. K. Doylend, M. J. R. Heck, J. D. Peters, M. L. Davenport, J. T. Bovington, L. A. Coldren, and J. E. Bowers, "Fully Integrated Hybrid Silicon Two Dimensional Beam Scanner", Optics Express, vol. 23, No. 5 doi:10.1364/OE.23.005861, p. 5861-5874; Feb. 25, 2015.
Brian W. Krause, Bruce G. Tiemann, and Philip Gatt, "Motion Compensated Frequency Modulated Continuous Wave 3D Coherent Imaging Ladar with Scannerless Architecture," Appl. Opt., 51, pp. 8745-8761 (2012).
Fei Ding, Zhuoxian Wang, Sailing He, Vladimir M. Shalaev, and Alexander V. Kildishev, "Broadband High-Efficiency Half-Wave Plate: A Supercell-Based Plasmonic Metasurface Approach", ACS Nano, doi: 10.1021/acsnano.5b00218, 2015.
Hooman Abediasl and Hossein Hashemi, "Monolithic optical phased-array transceiver in a standard SOI CMOS process", Opt. Express 23, 6509, doi: 10.1364/OE.23.006509, 2015.
David N. Hutchison, Jie Sun, Jonathan K. Doylend, Ranjeet Kumar, John Heck, Woosung Kim, Christopher T. Phare, Avi Feshali, and Haisheng Rong, "High-resolution aliasing-free optical beam steering", Optica 3, 887, doi: 10.1364/OPTICA.3.000887, 2016.
Firooz Aflatouni, Behrooz Abiri, Angad Rekhi, and Ali Hajimiri, "Nanophotonic coherent imager", Opt. Express 23, doi: 10.1364/OE.23.005117, 2015.
Tin Komljenovic, Roger Helkey, Larry Coldren, and John E. Bowers, "Sparse aperiodic arrays for optical beam forming and LIDAR", Opt. Express 25, 2511, doi: 10.1364/OE.25.002511, 2017.
Binbin Guan, Ryan P. Scott, Chuan Qin, Nicolas K. Fontaine, Tiehui Su, Carlo Ferrari, Mark Cappuzzo, Fred Klemens, Bob Keller, Mark Earnshaw, and S. J. B. Yoo, "Free-space coherent optical communication with orbital angular, momentum multiplexing/demultiplexing using a hybrid 3D photonic integrated circuit", Opt. Express 22, 145, doi: 10.1364/OE.22.000145, 2014.
William S. Rabinovich ; Peter G. Goetz ; Marcel Pruessner ; Rita Mahon ;Mike S. Ferraro ; Doe Park ; Erin Fleet ; Michael J. DePrenger, "Free space optical communication link using a silicon photonic optical phased array", Proc. SPIE 9354, 93540B, doi:10.1117/12.2077222, 2015.
J. Sun, "Toward accurate and large-scale silicon photonics," MIT Ph.D. Thesis, 2013.
Ami Yaacobi, Jie Sun, Michele Moresco, Gerald Leake, Douglas Coolbaugh, and Michael R. Watt, "Integrated phased array for wide-angle beam steering", Opt. Lett. 39, 4575, doi: 10.1364/OL. 39.004575, 2014.
Christopher V. Poulton, Matthew J. Byrd, Manan Raval, Zhan Su, Nanxi Li, Erman Timurdogan, Douglas Coolbaugh, Diedrik Vermeulen, and Michael R. Watts, "Large-scale silicon nitride nanophotonic phased arrays at infrared and visible wavelengths", Optics Letters, v. 42, No. 1, doi: 10.1364/OL.42.000021, 2017.
Christopher V. Poulton, Ami Yaccobi, Zhan Su, Matthew J. Byrd, and Michael R. Watts, "Optical Phased Array with Small Spot Size, High Steering Range and Grouped Cascaded Phase Shifters", Advanced Photonics 2016, OSA technical Digest, paper IW1B.2, doi: 10.1364/IPRSN.2016.IW1B.2, 2016.
Manan Raval, Ami Yaacobi, Daniel Coleman, Nicholas M. Fahrenkopf, Christopher Baiocco, Gerald Leake, Thomas N. Adam, Douglas Coolbaugh, and Michael R. Watts, "Nanophotonic Phased Array for Visible Light Image Projection", in IEEE Photonics Conference (2016), paper MG3.4, doi: 10.1109/IPCon.2016.7831042, 2016.
K. K. Mehta and R. J. Ram, "Precise and diffraction-limited waveguide-to-free-space focusing gratings," arXiv 1607.00107, 2016.
David Fattal, Zhen Peng, Tho Tran, Sonny Vo, Marco Fiorentino, Jim Brug & Raymond G. Beausoleil, "A multi-directional backlight for a wide-angle, glasses-free three-dimensional display", Nature 495, 348, 2013.

(56) References Cited

OTHER PUBLICATIONS

Martijn J. R. Heck, "Highly integrated optical phased arrays: photonic integrated circuits for optical beam shaping and beam steering", Nanophotonics, 6(1): 93-107, doi: 10.1515/nanoph-2015-0152, 2017.
Trevor K. Chan, Mischa Megens, Byung-Wook Yoo, John Wyras, Connie J. Chang-Hasnain, Ming C. Wu, and David A. Horsley, "Optical beamsteering using an 8 × 8 MEMS phased array with closed-loop interferometric phase control", Opt Express; 21:2807-15, 2013.

* cited by examiner

INTEGRATED PHOTONIC ARRAY FED BY FREE-SPACE OPTICS

RELATED APPLICATION SECTION

The present application is a non-provisional of copending U.S. Provisional Patent Application Ser. No. 62/525,783, filed Jun. 28, 2017, and entitled "Integrated Photonic Array Fed by Free-Space Optics." The entire content of U.S. Patent Application Ser. No. 62/525,783 is incorporated herein by reference.

The section headings used herein are for organizational purposes only and should not to be construed as limiting the subject matter described in the present application in any way.

INTRODUCTION

There are numerous applications of optical phased arrays including medical imaging and therapy, Light Detection and Ranging (LiDAR), and various types of optical sensors. These various applications benefit from the availability of small size, low-cost, high-speed, and high-device-density optical phased arrays. As such, the use of photonic integration to reduce size and cost and to increase the density and complexity of available devices will speed the adoption of optical phased array technologies to support these applications.

DESCRIPTION OF VARIOUS EMBODIMENTS

Figure 1B:
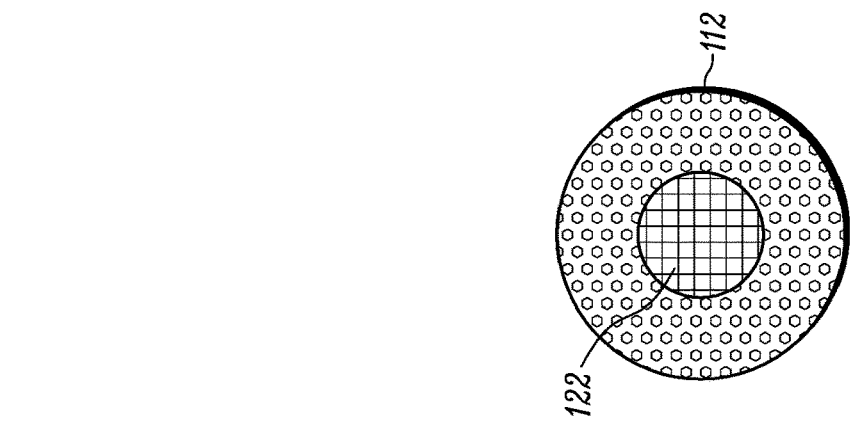
FIG. 1B illustrates a front-view of the embodiment of the integrated photonic phased array described in connection with FIG. 1A.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teaching may be performed in any order and/or simultaneously as long as the teaching remains operable. Furthermore, it should be understood that the apparatus and methods of the present teaching can include any number or all of the described embodiments as long as the teaching remains operable.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

There are numerous applications of optical phased arrays including medical imaging and therapy, LiDAR, and various types of optical sensors. Photonic integration allows the opportunity for small size, low-cost, high-speed, and a larger number of elements in the array. Photonic integrated devices are also referred to as photonic integrated circuits (PICs). Photonic materials used to construct photonic integrated circuits include silicon photonics, InP, GaAs and others. Most approaches to photonic integrated optical phased arrays, or PIC phased arrays, use optical- and electrical-waveguide feed networks in the same plane (or nearly the same plane and connected via VIAs or other structures) as the antenna elements. Confining the structure of the phased array to substantially a planar surface area and using waveguide feeds can be problematic for many reasons including, for example, creating a low antenna area fill factor, large element-to-element spacing, excessive optical waveguide, splitting excess losses, optical and electrical cross talk, antenna side lobe issues, and/or limited scan angles. This is, in part, due to the space required for waveguide routing of light from the transmitter, TX, or receiver, RX, to and from the antenna elements. It is also due to the space needed for electrical contacts to and from the antenna elements. Using free space illumination of an optical array, in a reflection or a transmission mode, eliminates some of the space and complexity as compared to a waveguide feed structure for photonic emitters. The optical phased array directs the free space optical beam based on the amplitude and phase profile provided by the array to the optical beam over the illuminated region of the array. This directing of the free space optical beam may operate in transmission and/or reflection. Using free space illumination of an optical array also allows higher fill factors and has other benefits.

One feature of the present teaching is the use of free-space optics to propagate optical beams to the surface of a PIC phased array to provide a combination of the benefits of using PICs, with the benefits of free-space optical configurations for phased array illumination. FIG. 1A illustrates a block diagram of an embodiment of an integrated photonic phased array system 100 that does not use a waveguide feed structure but rather, uses free space illumination. A laser source 102 (or other type of optical source or signal) is coupled to an optical circulator 104. In some embodiments, the laser source 102 is a fiber coupled laser source. The optical circulator 104 may be fiber coupled also it is possible not to use an optical circulator and use items such as beam splitters. The output of the circulator 104 is collimated by an optical element 106 and sent to one or more other optical elements 108. The other optical elements 108 may include, for example, lenses, beam shapers, polarizers, waveplates, or other known passive or active optical elements. The output of the optical elements 108 projects the laser light beam 110 toward a surface of a photonic phased array 112, thereby illuminating the surface of the photonic phased array 112. The optical elements 108 may also be configured to perform spatial tailoring or apodizing of the intensity profile of the laser light beam 110 to get a desired spatial profile across the surface of the photonic array 112. In some embodiments, the apodizing is reconfigurable, and in other embodiments, the apodizing is fixed, or static. The photonic phased array 112 may be dynamic, i.e. configured as a modulator of the input and output beams. The photonic phased array 112 may be static, i.e. configured to direct the input and output beams without change. In both dynamic and static configurations, the photonic phased array may be electronically controlled, e.g. to configure the static arrangement of the array and/or to perform modulation. In some embodiments, the photonic optical phased array 112 is configured in reflection.

In some embodiments, the photonic optical phased array 112 comprises an electrical substrate that allows fan-out of electrical signals, such that a size of a region comprising the fan-out connections is larger than a size of the photonic optical phased array. It is also possible, as described later, that the optical phased array could work in transmission. The light illuminating the surface of the photonic phased array 112 is reflected off of the phased array and sent toward optional additional electro-optical elements 114 that project the light toward a target 116. For example, the target could be a sample, medical tissue, an automobile, or any other material. These electro-optical elements 114 may include lenses, telescopes, beam scanners, filters, polarizers, or other known active or passive electro-optical elements. As shown by the arrows 118, the laser light beam 120 is scanned in various directions with respect to the target 116 and could also be scanned in a third dimensions (axial focus).

It should be noted that several alternative techniques exist in addition to angular spatial reflection separation off of the photonic phased array 112 illustrated in the embodiment of FIG. 1A. These alternative embodiments allow for different incident and reflected beam geometries. For example, some embodiments utilize normal incidence of incident light that are projected using non-polarizing beam splitters, polarizing beam splitter and wave plates, circulators, or other known optical elements. In some embodiments, the photonic phased array 112 is a photo-detector array and there is no incident or reflected signal and normal incidence can be used. In addition, in some embodiments the photonic phased array 112 works in transmission. In such embodiments, it may be beneficial if the substrate of array 112 is thinned to allow the light to have minimal losses.

Figure 1A:
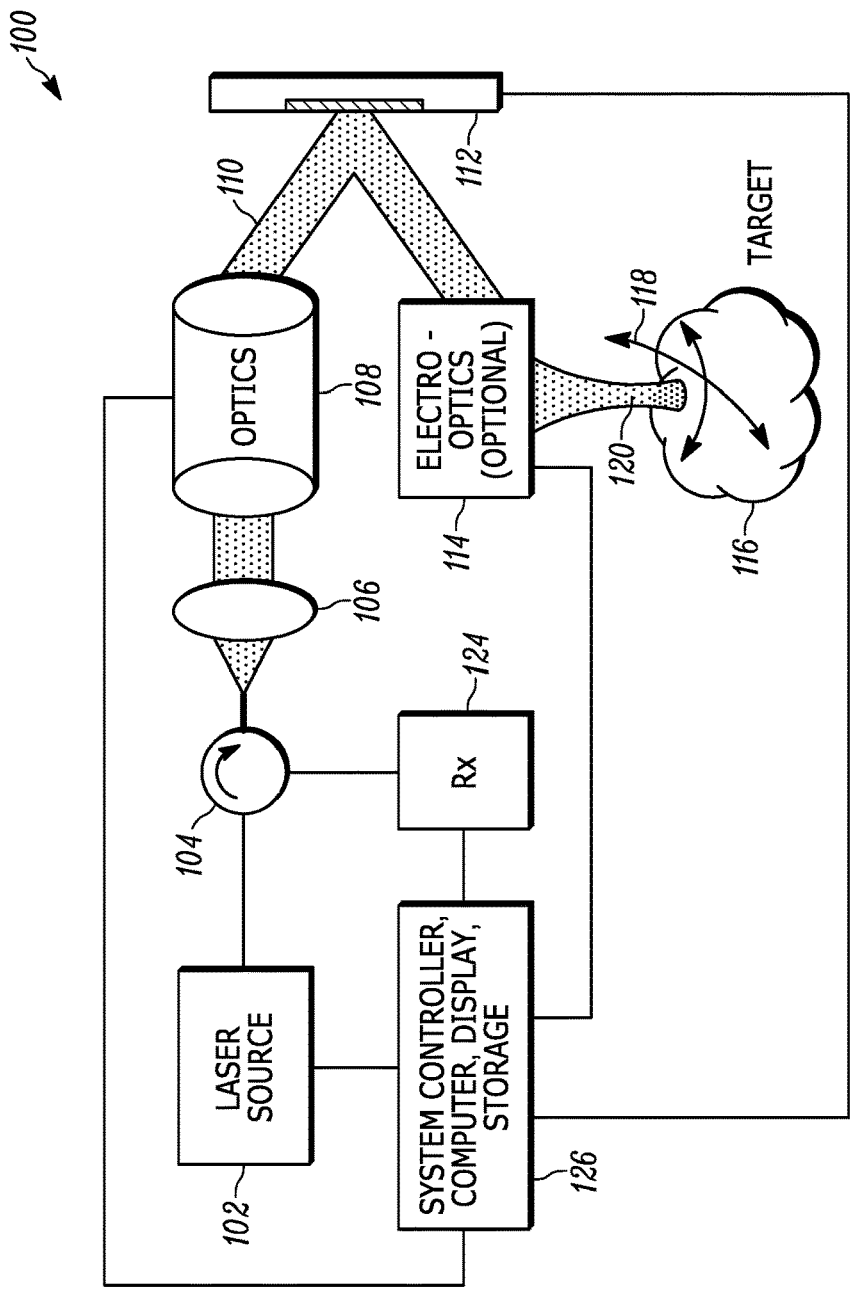
FIG. 1A illustrates a block diagram of an embodiment of an integrated photonic phased array that uses the free space illumination of the present teaching.

FIG. 1B illustrates a front-view of the embodiment of the integrated photonic phased array 112 described in connection with FIG. 1A. This embodiment includes a region 122 that reflects the incident laser light beam 110 with a particular amplitude and/or phase profile. The reflected light from the optical array can be simple angular scanning (as commonly used in LiDAR) or a more complex and arbitrary phase front can be implemented (e.g. for adaptive optics or multi-mode fiber endoscope applications). The integrated photonic phased array 112 can be for adjustment of phase only or for adjustment of both amplitude and phase. In applications, such as medical imaging or LiDAR, light back-reflected from the target, sample, or other material can be extracted to a port of a receiver 124 (Rx) via the circulator 104 as shown or using other similar optical transmit/receive separation techniques. The receiver 124 port may be fiber coupled. A system controller and/or computer display and/or storage system processor 126 may be optionally used to control any or all of the laser source 102, receiver 124, optical elements 108 that form and project the laser light beam 110, the photonic phased array 112, and/or the electro optic elements 114. The processor 126 is used, for example, for various known system control tasks, output processing, archive and display.

In many applications, it is desirable that the antenna elements in the integrated photonic phased array 112 are closely packed relative to a wavelength of operation of the laser source 102. Most existing techniques for optical phased arrays use dimensions that are much larger than a wavelength separation. The closely packed spacing allows for wider scanning angles due to the wider angular separation of the side lobes from the antenna array factor of the photonic phased array 112. In various embodiments, the photonic phased array 112 can be a 1D scanning array or the photonic phased array can be a 2D scanning array. In some embodiments, two 1D scanning arrays can be used in series to perform 2D scanning with appropriate optical elements in between, such as relay lenses. In some embodiments, two 1D arrays can be placed in close proximity (e.g. stacked) with no lenses in between. The photonic phased arrays typically consist of several elements, including, for example a substrate that can be electrically active or passive.

Figure 2:
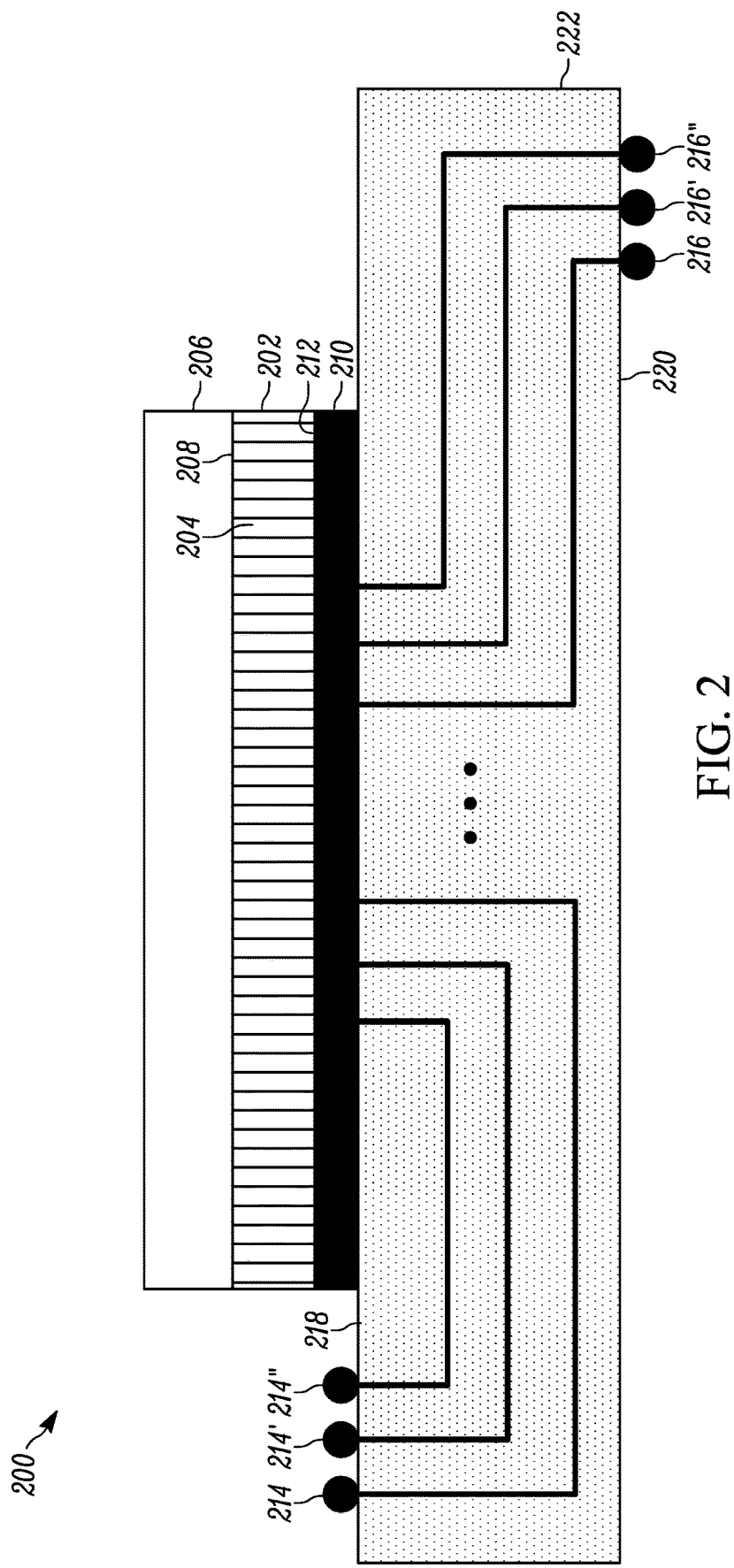
FIG. 2 illustrates an embodiment of an integrated optical photonic phased array suitable for operating in a reflective mode of the present teaching.

FIG. 2 illustrates an embodiment of an optical photonic phased array 200 suitable for operating in a reflective mode of the present teaching. There is an array layer 202 that includes an array of optical elements 204. The top section 206 can be an optically transparent but electrically conductive layer (e.g. transparent conducting film) to supply a common electrical signal to one side of the optical array elements 204. Alternatively, non-optical transparent electrical connections can run to each of the array elements 204 or run to each row (or column) of the array elements 204 at the expense of packing density of the array and implementation complexity (e.g. a fan-in). Below the top section 206 is the active photonic modulator array and/or detector array layer 202 such that a top side 208 of the elements 204 are in contact with the top layer 206. For example, this layer 202 could be a 2D array of silicon photonic electro-optical phase modulators operating in a surface reflectance mode. As part of, or below, the modulator/detector array layer 202 is a high reflectance layer 210 to reflect the incident light back toward the surface. Other embodiments achieve high reflectance by using grating structures that are either positioned separately or built into the modulator elements 204 or modulator layer 202 itself. There are a wide range of possible modulation techniques including thermal modulation, electro-optical modulation through PN junctions, and many others electro-optical, mechanical, or thermal effects that can be used for modulation.

There are a variety of ways to electrically connect to the bottom side 212 of the modular elements 204. The connections may be made individually to each element 204 in the array or the connections may be made to rows of elements or columns of elements of the array. For example, in many photonic integration technologies such as silicon photonics, InP, or GaAs, the photonic modulator layer 202 is fabricated to have many metal layers below the modulator elements 204. Those metal layers can be used to electrically fan-out the pitch of the tightly packed antenna phased array elements 204 to a wider area where there is more room to fabricate components like copper pillar bumps, die/ball bonds, bonding pads, and via technology. These various technologies can be used to make external fan-out electrical connections using substrate 222 via connectors 214, 214', 214'', 216, 216', 216'' that are located either on the same surface 218 as the modulator array layer 202 or the bottom surface 220. Both a same surface 218 set of fan-out connection connectors 214, 214', 214" and a bottom surface 220 set of fan-out connection connectors 216, 216', 216" is shown in FIG. 2 for illustration. In various embodiments, either a same surface 218 connection or a bottom surface 220 connection or a combination may be used. The metal layers can be connected in single ended fashion or using differential signals. If the bottom surface 220 electrical connection is desirable, then it is possible that the substrate can be thinned using etching, polishing, or other thinning techniques. In addition, in some embodiments vias (not shown) can be used to connect to die/ball bonds, pillars, or other suitable connection.

Various embodiments use various designs for the photonic modulator array 200. For example, a monolithic design can be used. Alternatively, multiple chips can be interconnected using interposers and/or flip-chip mounting, wafer bonding, or other techniques. The substrate 222 can also contain active electronic devices as well (e.g. TIAs, ADCs, DACs, Sample-holds, multiplexers, etc.) which typically occupy a space on the order of 100 micrometers by 100 micrometers (~100 µm×100 µm) that is much more than a wavelength and thus cannot be located directly under the active elements 204 of the photonic antenna array layer 202 due to space constraints.

Figure 3:
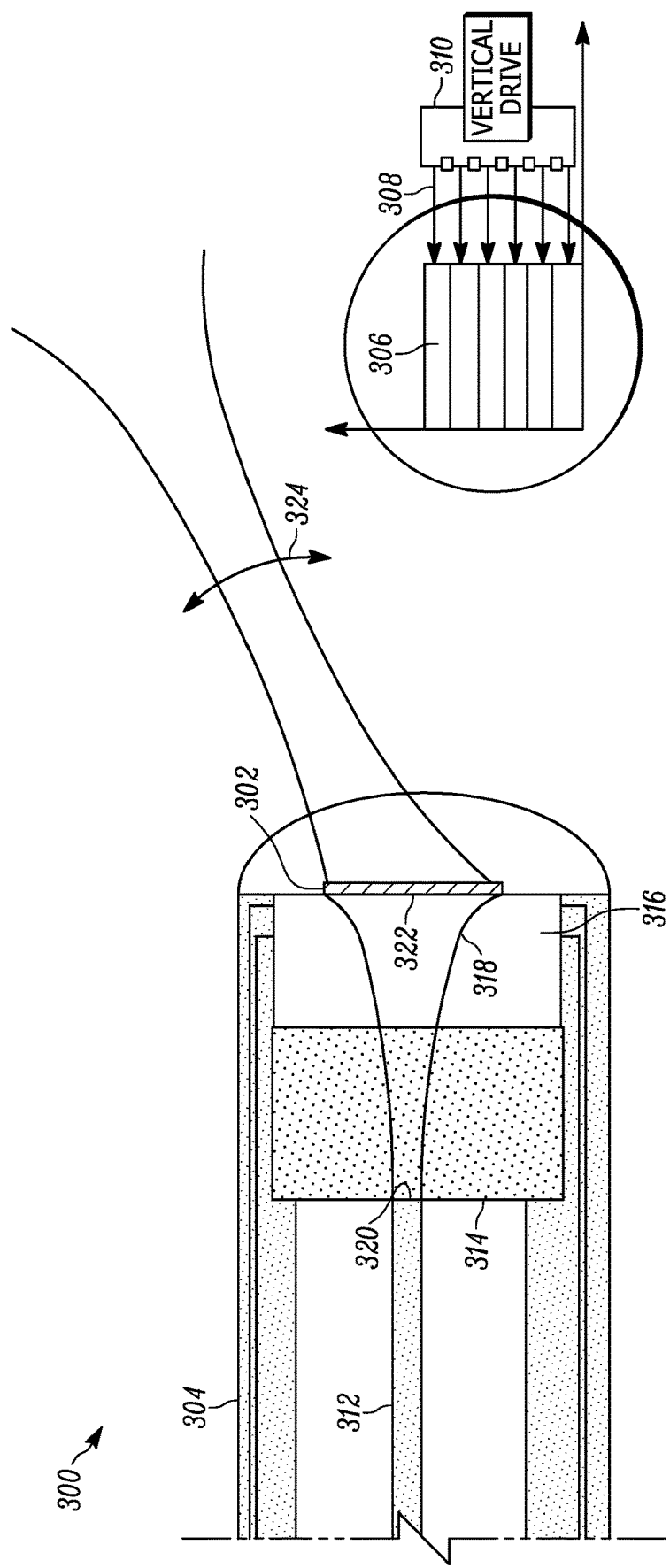
FIG. 3A illustrates an embodiment of a system that comprises an integrated photonic phased array device illuminated by free-space optics that are not fed by a waveguide structure.
FIG. 3B illustrates a front-view of an embodiment of an integrated phased array device of the present teaching.

FIG. 3A illustrates an embodiment of a system 300 that comprises a photonic phased array device 302 illuminated by free-space optics that are not fed by a waveguide structure. In this embodiment, the photonic phased array device 302 operates in transmission. The particular photonic phased array device 302 illustrated in FIG. 3A is an integrated optical phased array in an endoscopic application. This endoscope 304 could be coupled to an optical coherence tomography, Raman, NIR, or other types of optical endoscope medical imaging techniques (not shown). There are of course many non-medical applications such as LiDAR, optical communication, etc. These systems may operate in a receive, or reception, only configuration, where the illumination is provided from a target being measured. These systems may also operate in a transmit, or transmit and receive, or transceiver, configuration where illumination is supplied to and received from a target being measured.

There have been a variety of distal phased arrays proposed for tiny endoscopes including those using photonic integrated circuits (PICs). The majority of these PIC approaches have used an optical waveguide to feed a phased array. The disadvantage of using a waveguide feed, as described above, is that the optical (and/or electrical) feed causes a sparse aperture and wider than desired element spacing that leads to far field inefficiencies, limited scan angle, and a limited number of antenna elements.

FIG. 3B illustrates a front-view of an embodiment of a phased array device of the present teaching. The phased array elements 306 can include a single axis phased array (as shown in FIG. 3B) or, alternatively, two stacked single or one dual axis (2-axis) phased array. In the embodiment of FIG. 3B, each element has a drive input 308 that is supplied by a driver 310. The driver 310 may be located in various positions, and is connected to a controller that controls the drive signals. For example, the system controller can send individual electrical drives from the proximal end to each individual phase element at the distal end. Alternatively, instead of using individual drives to each phased array element, which increase cost and manufacturing complexity due to the large number of the electrical wires, in some embodiments there are fewer electronic drive signals (i.e. less than the number of phased elements) that are sent electrically down the endoscope to the distal end where there is a simple electrical circuit to perform signal conditioning used to create electrical connections to each element.

One feature of the optical systems of the present teaching is that an optical endoscope configured in transmission may be constructed. In some embodiments, the phased array is in electrical contact with a distal electrical conditioning circuit such that the number of a plurality of electrical wires configured down the endoscope is less than a number of elements in the phased array. For example, in the embodiment of FIGS. 3A-B, the electrical conditioning circuit is a simple electrical divider ladder using resistive structures feeding rows of modulators and is contained on the photonic integrated circuit (PIC) substrate that comprises the photonic phased array device 302. This approach can be used where simple angular scanning (e.g. linear) is desired. It is also possible in other embodiments to have a separate relatively simple electronic circuit in electrical communication with the photonic phased array device 302. In these embodiments, more complex electronic control of each phased array element 306 is possible than can be done with simple passive circuits. The phased array element 306 design alone, or in combination with the electrical signal conditioning structure can, in addition to the beam steering, also implement some or all of the focusing optics. In some embodiments, a separate focusing lens can be utilized and the phase array mainly implements wavefront angular scanning. In some embodiments, the phase tuning is electro-optical. In other embodiments, the phase tuning is thermally driven from heaters that heat individual elements 306.

As shown in FIG. 3A, a single mode fiber 312 runs along the housing of the endoscope. The fiber 312 interfaces with optional optical elements 314 and one or more structural elements 316, as shown. These elements 314, 316, in combination with the photonics circuit phased array device 302 itself, allow the beam 318 to expand from the fiber facet 320 to fill the phased array device 302 as desired. The desired optical thickness between the face 320 of the distal end of the single mode fiber and the phased array surface 322 is determined by known beam propagation equations.

In some embodiments, the desired beam waist dimension at the face of the phased array is determined from the desired focal length and beam waist 324 at focus in the sample/target (and any intermediate optics) and then that desired beam waist parameter is matched at the phase array from the field propagating from the single-mode fiber through the optics structure and the PIC substrate. These calculations to determine the beam waist are performed using known Gaussian and other optical propagation equations. As mentioned above, in most cases (e.g. for silicon photonic circuits operating at 1310 nm), it is important to thin the device after fabrication to remove substrate material reducing absorption of the light. In one embodiment, a transparent conducting film is applied to one side of the phased array and the other side has individual wired connections. The wired connections may be either transparent or not. Note the thinning of the substrate could take place only under the antenna elements themselves not the entire area (not shown).

One feature of the present teaching is that the photonic integrated PIC with free-space optical addressing and/or integrated electrical fan-in and/or fan-out connections can be used for optical scanning systems that operate in one, two and/or three dimensions using known scanning techniques. Various embodiments of the present teaching, for example, the embodiment illustrated in FIG. 3B, show a one-dimensional electrically-controlled phased array capable of scanning along, for example, a vertical axis. Those skilled in the art will appreciate that it is possible for the phased array to have steering in one direction, as shown in, for example, FIG. 3B, together with a wavelength sensitive structure in the other dimension (e.g. along the horizontal phased array elements) to allow steering of the optical beam in two dimensions. In general, some embodiments of the present teaching utilize an electrically-controlled phase array to steer in one direction, and utilize a tunable wavelength optical source to provide steering of the beam in another, in some cases orthogonal, direction.

Figure 4:
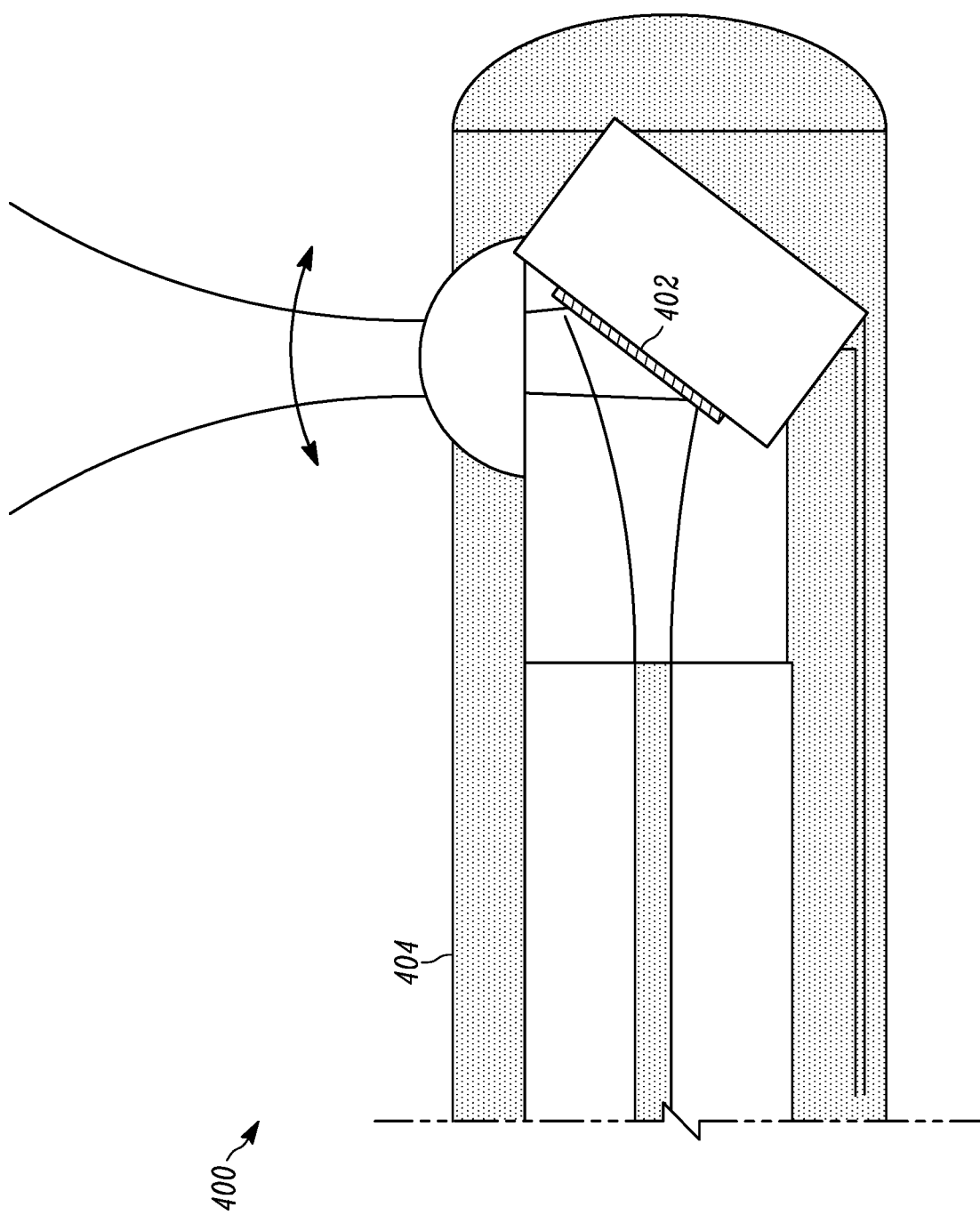
FIG. 4 illustrates an embodiment of an optical endoscope system with an integrated phased array device operating in reflection of the present teaching.

Another feature of the present teaching is that an optical endoscope that utilizes an integrated photonic phased array configured in reflection may be constructed where the phased array is in electrical contact with a distal electrical ladder network such that a number of electrical wires running down the endoscope is less than a number of elements in the phased array. FIG. 4 illustrates an embodiment of an optical endoscope system 400 with a phased array device 402 operating in reflection of the present teaching. It is possible to make an optical endoscope 404 with a phased array device 402 operating in reflection by positioning the phased array device 402 so as to operate in a side imaging mode as shown in FIG. 4. In this configuration, the optics could be free space to allow the light to freely propagate.

EQUIVALENTS

While the applicant's teaching are described in conjunction with various embodiments, it is not intended that the applicant's teaching be limited to such embodiments. On the contrary, the applicant's teaching encompasses various alternatives, modifications, and equivalents, as will be appreciated by those of skill in the art, which may be made therein without departing from the spirit and scope of the teaching.

What is claimed is:

1. An optical system that produces an optical probe beam, the optical system comprising:
    a) an optical element positioned in a path of a free-space optical beam to project the free-space optical beam to generate a projected free-space optical beam; and
    b) a photonic integrated phased-array component positioned in a path of the projected free-space optical beam to direct the projected free space optical beam, thereby generating the optical probe beam, the photonic integrated phased-array component comprising a plurality of antenna elements and a substrate positioned proximate to the plurality of antenna elements, wherein the substrate includes a plurality of fan-out electrical connections from at least some of the plurality of antenna elements such that a size of a region comprising the fan-out electrical connections is larger than a size of a region comprising the plurality of antenna elements.

2. The optical system for producing the optical probe beam of claim 1 further comprising an electro-optical element positioned in the path of the optical probe beam.

3. The optical system for producing the optical probe beam of claim 1 further comprising a receiver having an input that receives a portion of light from the optical probe beam that is reflected by the target.

4. The optical system for producing the optical probe beam of claim 3 wherein the received portion of light is reflected by the photonic integrated phased-array device.

5. The optical system for producing the optical probe beam of claim 1 wherein the photonic integrated phased-array component comprises a silicon-photonics photonic integrated circuit component.

6. The optical system for producing the optical probe beam of claim 1 wherein the photonic integrated phased-array component comprises an InP photonic integrated circuit component.

7. The optical system for producing the optical probe beam of claim 1 wherein the photonic integrated phased-array component comprises a GaAs photonic integrated circuit component.

8. The optical system for producing the optical probe beam of claim 1 wherein the photonic integrated phased-array component further comprises a transparent conducting layer proximate to the plurality of antenna elements.

9. The optical system for producing the optical probe beam of claim 1 wherein the optical element performs spatial tailoring of the projected optical beam that generates a desired spatial profile at a surface of the photonic integrated phased-array component.

10. The optical system for producing the optical probe beam of claim 1 wherein the optical element performs apodizing of the projected optical beam to generate a desired spatial profile of the projected optical beam at a surface of the photonic integrated phased-array component.

11. The optical system for producing the optical probe beam of claim 1 wherein the optical element comprises a lens.

12. The optical system for producing the optical probe beam of claim 1 wherein the optical element comprises a beam shaper.

13. The optical system for producing the optical probe beam of claim 1 wherein photonic integrated phased-array component comprises a modulator array.

14. The optical system for producing the optical probe beam of claim 1 wherein photonic integrated phased-array component comprises a detector array.

15. The optical system for producing the optical probe beam of claim 1 wherein the target is a sample to analyzed.

16. The optical system for producing the optical probe beam of claim 1 further comprising an optical source that generates the free-space optical beam.

17. An optical endoscope comprising:
    a) a plurality of electrical wires connecting a proximal end of the optical endoscope to a distal end of the optical endoscope;
    b) a photonic integrated phased-array component positioned at the distal end of the optical endoscope in a path of a free-space optical beam, the photonic integrated phased-array component comprising a plurality of antenna elements;
    c) a target in the path of the free-space optical beam; and
    d) an electrical conditioning circuit electrically connected between an electrical output of at least some of the plurality of antenna elements and the plurality of electrical wires such that a number of the plurality of electrical wires connected the proximal end of the optical endoscope to the distal end of the optical endoscope is less than a number of the plurality of antenna elements.

18. The optical endoscope of claim 17 wherein the photonic integrated phased-array component comprises a transmissive photonic integrated phased-array component.

19. The optical endoscope of claim 17 wherein the photonic integrated phased-array component comprises a reflective photonic integrated phased-array component.

20. The optical endoscope of claim 19 wherein the optical endoscope is configured to operate in a side imaging application.

21. The optical endoscope of claim 17 wherein the photonic integrated phased-array component further comprises a transparent conducting layer proximate to the plurality of antenna elements.

22. The optical endoscope of claim 17 wherein the photonic integrated phased-array component further comprises a substrate positioned proximate to the plurality of antenna elements, wherein the substrate is configured to provide a plurality of fan-out electrical connections from at least some of the plurality of antenna elements such that a size of a region comprising the fan-out electrical connections is larger than a size of a region comprising the plurality of antenna elements.

23. The optical endoscope of claim 17 wherein the electrical conditioning circuit comprises a ladder network.

24. The optical endoscope of claim 17 wherein the photonic integrated phased-array component is configured to direct the free space optical beam to the target.

25. The optical endoscope of claim 17 wherein the photonic integrated phased-array component is configured to direct the free space optical beam from the target.

\* \* \* \* \*